United States Patent
Moller

(10) Patent No.: US 9,977,029 B2
(45) Date of Patent: May 22, 2018

(54) DIAGNOSTIC BLOOD TEST FOR SARCOIDOSIS

(71) Applicant: David R. Moller, Ellicott City, MD (US)

(72) Inventor: David R. Moller, Ellicott City, MD (US)

( * ) Notice: Subject to any disclaimer, the term of this patent is extended or adjusted under 35 U.S.C. 154(b) by 54 days.

(21) Appl. No.: 14/937,423

(22) Filed: Nov. 10, 2015

(65) Prior Publication Data

US 2016/0139145 A1     May 19, 2016

Related U.S. Application Data

(62) Division of application No. 14/279,591, filed on May 16, 2014.

(60) Provisional application No. 61/924,410, filed on Jan. 7, 2014.

(51) Int. Cl.
| | | |
|---|---|---|
| *G01N 33/00* | (2006.01) | |
| *C12M 3/00* | (2006.01) | |
| *G01N 33/68* | (2006.01) | |

(52) U.S. Cl.
CPC ..... *G01N 33/6866* (2013.01); *G01N 2333/57* (2013.01); *G01N 2800/24* (2013.01); *G01N 2800/7095* (2013.01)

(58) Field of Classification Search
None
See application file for complete search history.

(56) References Cited

U.S. PATENT DOCUMENTS

2009/0175798 A1*   7/2009   Moller ................. A61K 38/44
                                                                         424/9.81

OTHER PUBLICATIONS

Kolchanov, 1988, Journal of Molecular Evolution, vol. 27, pp. 154-162.*
Pasquo, 2012, PLoS ONE, vol. 7, Issue 2, e32555.*
Jacobs et al. (1997), J. Immunol., vol. 118, pp. 21-27.*
Chen, E. et al. "T Cell Responses to Mycobacterial Catalase-Peroxidase Profile of Pathogenic Antigen is Systemic Sarcoidosis", The Journal of Immunology (Dec. 2008).
Johnsson, W. et al "Enzymology: Overexpression, Purification, and Characterization of the Catalase-Peroxidase KatG from *Mycobacterium tuberculosis*" The Journal of Biological Chemistry, vol. 272, No. 5, pp. 2834-2840, (Jan. 1997).
Matsumoto, M. et al. "Lipopolysaccharide-Binding Peptides Obtained by Phage Display Method" Journal of Microbiological Methods, vol. 82, pp. 55-58, (Apr. 2010).
Song, Z. et al. "Mycobacterial Catalase-Peroxidase is a Tissue Antigen and Target of the Adaptive Immune Response in Systemic Sarcoidosis" The Journal of Experimental Medicine, vol. 201, No. 5, pp. 755-767, (Mar. 2005).
Zhang, Y. et al. "The Catalase-Peroxidase Gene and Isoniazid Resistance of *Mycobacterium tuberculosis*" Nature, vol. 358, (Aug. 1992).

* cited by examiner

*Primary Examiner* — Vanessa L. Ford
*Assistant Examiner* — Jegatheesan Seharaseyon
(74) *Attorney, Agent, or Firm* — Meagher Emanuel Laks Goldberg & Liao, LLP.

(57) ABSTRACT

Sarcoidosis is a multisystem disease characterized by granulomatous inflammation in affected organs. The present invention discloses kits and a system for a blood test using mycobacterial catalase-peroxidase that has a high positive predictive value for confirming a diagnosis of sarcoidosis.

2 Claims, 1 Drawing Sheet

TABLE 1
rec-mKatG/PPD

|   | media/PM | mKatG | PPD | Result |   |   | media/PM | mKatG | PPD | Result |
|---|---|---|---|---|---|---|---|---|---|---|
| 1 | 37 | 199 | 150 | pos | 1 | lung ca | 57 | 76 | 1097 | neg |
| 2 | 294 | 452 | 387 | pos | 2 | lung mass | 57 | 107 | 301 | neg |
| 3 | 73 | 66 | 210 | neg | 3 | lung ca | 40 | 347 | 1024 | neg |
| 4 | 51 | 61 | 439 | neg | 4 | psoriasis | 53 | 71 | 152 | neg |
| 5 | 125 | 335 | 191 | pos | 5 | lung ca | 44 | 48 | 281 | neg |
| 6 | 103 | 150 | 2114 | neg | 6 | ALI with | 0 | 846 | 4739 | neg |
| 7 | 97 | 964 | 286 | pos | 7 | lung nodule | 0 | 0 | 103 | neg |
| 8 | 60 | 1091 | 73 | pos | 8 | HP | 0 | 0 | 63 | neg |
| 9 | 59 | 466 | 356 | pos | 9 | BCG | 46 | 0 | 665 | neg |
| 10 | 110 | 1227 | 278 | pos | 10 | BCG | 5 | 0 | nd | neg |
| 11 | 56 | 1205 | 236 | pos | 11 | PPD+ | 29 | 2 | nd | neg |
| 12 | 75 | 332 | 144 | pos | 12 | healthy | 0 | 0 | nd | neg |
| 13 | 9 | 172 | 19 | pos | 13 | healthy | 0 | 0 | nd | neg |
| 14 | 0 | 6 | 52 | neg | 14 | Trach sten | 0 | 0 | 899 | neg |
| 15 | 33 | 30 | 33 | neg | 15 | anti-PLS | 34 | 28 | 350 | neg |
| 16 | 36 | 48 | 629 | neg | 16 | M abscess | 0 | 0 | 129 | neg |
| 17 | 45 | 606 | 62 | pos | 17 | cardiomyopathy | 0 | 0 | 0 | neg |
| 18 | 91 | 205 | 435 | neg | 18 | BCG | 0 | 0 | 0 | neg |
| 19 | 23 | 28 | 36 | neg | 19 | lung ca vs other | 44 | 43 | 535 | neg |
| 20 | 28 | 2647 | 347 | pos | 20 | healthy | 85 | 90 | 82 | neg |
| 21 | 30 | 836 | 93 | pos | 21 | BCG | 62 | 302 | 2005 | neg |
| 22 | 116 | 297 | 154 | pos | 22 | BCG+PPD+ | 34 | 128 | 180 | neg |
| 23 | 32 | 871 | 39 | pos | 23 | BCG+PPD+ | 21 | 57 | 495 | neg |
| 24 | 66 | 73 | 66 | neg | 24 | BCG+PPD+ | 71 | 103 | 2225 | neg |
| 25 | 21 | 2282 | 173 | pos | 25 | BCG+PPD+ | 211 | 224 | 2429 | neg |
| 26 | 39 | 1604 | 48 | pos | 26 | BCG | 214 | 407 | 1995 | neg |
| 27 | 34 | 293 | 63 | pos | 27 | BCG | 27 | 31 | 1785 | neg |
| 28 | 140 | 1065 | 204 | pos | 28 | BCG | 22 | 124 | 1023 | neg |
| 29 | 99 | 969 | 188 | pos | 29 | GPA | 19 | 17 | 12 | neg |
| 30 | 23 | 37 | 44 | neg | 30 | lung nodule | 16 | 21 | 1117 | neg |
| 31 | 36 | 282 | 1835 | neg | 31** | ~~healthy~~ | ~~18~~ | ~~489~~ | ~~47~~ | ~~pos~~ |
|   |   |   |   |   | 32 | BCG | 23 | 316 | 2213 | neg |
| Sarcoidosis Inactive |   |   |   |   | 33 | BCG | 22 | 1719 | 2369 | neg |
| 32 | 18 | 21 | 26 | neg | 34 | BCG | 30 | 249 | 341 | neg |
| 33 | 0 | 0 | 4 | neg | 35 | BCG | 30 | 483 | 4353 | neg |
| Sarcoidosis Treated |   |   |   |   | 36 | healthy | 38 | 64 | 91 | neg |
| 34 | 24 | 25 | 22 | neg | 37 | PPD+ | 36 | 442 | 945 | neg |
| 35 | 15 | 31 | 31 | neg | 38 | lung infiltrates | 66 | 1449 | >2500 | neg |
| 36 | 18 | 489 | 47 | pos | 39 | lung ca | 104 | 258 | 127 | pos |
| 37 | 33 | 101 | 104 | neg | 40 | breast ca | 15 | 84 | 764 | neg |
| 38 | 54 | 74 | 88 | neg | 41 | ca | 18 | 22 | 16 | neg |
| 39 | 20 | 51 | 90 | neg | 42 | myocarditis | 22 | 46 | 95 | neg |
| 40 | 16 | 14 | 17 | neg |   |   |   |   |   |   |
|   |   |   |   |   | 1247 | health 29 | 6000 | 982 | 5977 | Test discarded* |
|   |   |   |   |   | 1249 | health 45 | 5835 | 540 | 6052 | Test discarded |

\* mKatG near SEA/SEB positive controls, presumed contamination
\*\* inserted by mistake in original presentation

SEQUENCE LISTING

```
<160> NUMBER OF SEQ ID NOS: 2

<210> SEQ ID NO 1
<211> LENGTH: 13
<212> TYPE: PRT
<213> ORGANISM: Artificial Sequence
<220> FEATURE:
<223> OTHER INFORMATION: LPS and/or lipid A binding peptide

<400> SEQUENCE: 1

Lys Asn Tyr Ser Ser Ser Ile Ser Ser Ile His Ala Cys
1               5                   10

<210> SEQ ID NO 2
<211> LENGTH: 740
<212> TYPE: PRT
<213> ORGANISM: Mycobacterium tuberculosis
```

<400> SEQUENCE: 2

```
Met Pro Glu Gln His Pro Pro Ile Thr Glu Thr Thr Thr Gly Ala Ala
1               5                   10                  15

Ser Asn Gly Cys Pro Val Val Gly His Met Lys Tyr Pro Val Glu Gly
            20                  25                  30

Gly Gly Asn Gln Asp Trp Trp Pro Asn Arg Leu Asn Leu Lys Val Leu
        35                  40                  45

His Gln Asn Pro Ala Val Ala Asp Pro Met Gly Ala Ala Phe Asp Tyr
    50                  55                  60

Ala Ala Glu Val Ala Thr Ile Asp Val Asp Ala Leu Thr Arg Asp Ile
65                  70                  75                  80

Glu Glu Val Met Thr Thr Ser Gln Pro Trp Trp Pro Ala Asp Tyr Gly
                85                  90                  95

His Tyr Gly Pro Leu Phe Ile Arg Met Ala Trp His Ala Ala Gly Thr
            100                 105                 110

Tyr Arg Ile His Asp Gly Arg Gly Ala Gly Gly Gly Met Gln Arg
            115                 120                 125

Phe Ala Pro Leu Asn Ser Trp Pro Asp Asn Ala Ser Leu Asp Lys Ala
    130                 135                 140

Arg Arg Leu Leu Trp Pro Val Lys Lys Lys Tyr Gly Lys Lys Leu Ser
145                 150                 155                 160

Trp Ala Asp Leu Ile Val Phe Ala Gly Asn Cys Ala Leu Glu Ser Met
                165                 170                 175

Gly Phe Lys Thr Phe Gly Phe Gly Phe Gly Arg Val Asp Gln Trp Glu
            180                 185                 190

Pro Asp Glu Val Tyr Trp Gly Lys Glu Ala Thr Trp Leu Gly Asp Glu
        195                 200                 205

Arg Tyr Ser Gly Lys Arg Asp Leu Glu Asn Pro Leu Ala Ala Val Gln
    210                 215                 220

Met Gly Leu Ile Tyr Val Asn Pro Glu Gly Pro Asn Gly Asn Pro Asp
225                 230                 235                 240

Pro Met Ala Ala Ala Val Asp Ile Arg Glu Thr Phe Arg Arg Met Ala
                245                 250                 255

Met Asn Asp Val Glu Thr Ala Ala Leu Ile Val Gly Gly His Thr Phe
            260                 265                 270

Gly Lys Thr His Gly Ala Gly Pro Ala Asp Leu Val Gly Pro Glu Pro
        275                 280                 285

Glu Ala Ala Pro Leu Glu Gln Met Gly Leu Gly Trp Lys Ser Ser Tyr
    290                 295                 300

Gly Thr Gly Thr Gly Lys Asp Ala Ile Thr Thr Gly Ile Glu Val Val
305                 310                 315                 320

Trp Thr Asn Thr Pro Thr Lys Trp Asp Asn Ser Phe Leu Glu Ile Leu
                325                 330                 335

Tyr Gly Tyr Glu Trp Glu Leu Thr Lys Ser Pro Ala Gly Ala Trp Gln
            340                 345                 350

Tyr Thr Ala Lys Asp Gly Ala Gly Ala Gly Thr Ile Pro Asp Pro Phe
        355                 360                 365

Gly Gly Pro Gly Arg Ser Pro Thr Met Leu Ala Thr Asp Leu Ser Leu
    370                 375                 380

Arg Val Asp Pro Ile Tyr Glu Arg Ile Thr Arg Arg Trp Leu Glu His
385                 390                 395                 400

Pro Glu Glu Leu Ala Asp Glu Phe Ala Lys Ala Trp Tyr Lys Leu Ile
                405                 410                 415
```

```
His Arg Asp Met Gly Pro Val Ala Arg Tyr Leu Gly Pro Leu Val Pro
            420                 425                 430

Lys Gln Thr Leu Leu Trp Gln Asp Pro Val Pro Ala Val Ser His Asp
            435                 440                 445

Leu Val Gly Glu Ala Glu Ile Ala Ser Leu Lys Ser Gln Ile Arg Ala
    450                 455                 460

Ser Gly Leu Thr Val Ser Gln Leu Val Ser Thr Ala Trp Ala Ala Ala
465                 470                 475                 480

Ser Ser Phe Arg Gly Ser Asp Lys Arg Gly Ala Asn Gly Gly Arg
                485                 490                 495

Ile Arg Leu Gln Pro Gln Val Gly Trp Glu Val Asn Asp Pro Asp Gly
            500                 505                 510

Asp Leu Arg Lys Val Ile Arg Thr Leu Glu Glu Ile Gln Glu Ser Phe
            515                 520                 525

Asn Ser Ala Ala Pro Gly Asn Ile Lys Val Ser Phe Ala Asp Leu Val
    530                 535                 540

Val Leu Gly Gly Cys Ala Ala Ile Glu Lys Ala Ala Lys Ala Ala Gly
545                 550                 555                 560

His Asn Ile Thr Val Pro Phe Thr Pro Gly Arg Thr Asp Ala Ser Gln
                565                 570                 575

Glu Gln Thr Asp Val Glu Ser Phe Ala Val Leu Glu Pro Lys Ala Asp
            580                 585                 590

Gly Phe Arg Asn Tyr Leu Gly Lys Gly Asn Pro Leu Pro Ala Glu Tyr
            595                 600                 605

Met Leu Leu Asp Lys Ala Asn Leu Leu Thr Leu Ser Ala Pro Glu Met
            610                 615                 620

Thr Val Leu Val Gly Gly Leu Arg Val Leu Gly Ala Asn Tyr Lys Arg
625                 630                 635                 640

Leu Pro Leu Gly Val Phe Thr Glu Ala Ser Glu Ser Leu Thr Asn Asp
                645                 650                 655

Phe Phe Val Asn Leu Leu Asp Met Gly Ile Thr Trp Glu Pro Ser Pro
            660                 665                 670

Ala Asp Asp Gly Thr Tyr Gln Gly Lys Asp Gly Ser Arg Lys Val Lys
            675                 680                 685

Trp Thr Gly Ser Arg Val Asp Leu Val Phe Gly Ser Asn Ser Glu Leu
            690                 695                 700

Arg Ala Leu Val Glu Val Tyr Gly Ala Asp Asp Ala Gln Pro Lys Phe
705                 710                 715                 720

Val Gln Asp Phe Val Ala Ala Trp Asp Lys Val Met Asn Leu Asp Arg
                725                 730                 735

Phe Asp Val Arg
            740
```

DIAGNOSTIC BLOOD TEST FOR SARCOIDOSIS

CROSS-REFERENCE TO PRIOR FILED APPLICATIONS

This application is a divisional application of co-pending U.S. application Ser. No. 14/279,591, and claims the benefit of U.S. Provisional Application No. 61/924,410 filed Jan. 7, 2014. The disclosure of U.S. patent application Ser. No. 14/279,591 is expressly incorporated by reference herein in its entirety. Also, the Sequence Listing filed electronically herewith is also hereby incorporated by reference in its entirety (File Name: DM-103 ST25 Sequence Listing.txt; Date Created: Nov. 14, 2017; File Size: 6.7 KB.)

STATEMENT REGARDING FEDERALLY SPONSORED RESEARCH OR DEVELOPMENT

This invention was made with government support under Grant Nos. P50 HL107185 and R01 HL083870 awarded by the National Heart, Lung, and Blood Institute (NHLBI) of the National Institutes of Health. The government has certain rights in the invention.

TECHNICAL FIELD

This present disclosure generally relates to systems for detecting Sarcoidosis.

BACKGROUND OF THE INVENTION

Sarcoidosis is a multisystem disease characterized by granulomatous inflammation in affected organs. There are no useful biomarkers to confirm a diagnosis of sarcoidosis. A consensus among the medical community is that there is no blood test with sufficient specificity and sensitivity to be useful as a diagnostic test. Confirmation of a diagnosis of sarcoidosis in most cases requires a biopsy with its attendant risks and costs.

Using a proteomic approach, mKatG has been identified as a tissue antigen and target of the immune response in sarcoidosis (J. Exp. Med. (2005) 201:755-67; U.S. Pat. Appl. Pub. No. US 2009/0175798). An immunoassay was used to identify T cell responses to mKatG and this allowed the detection of a secreted cytokine, interferon-gamma (INFγ), in response to mKatG. However, this immunoassay, using INFγ-ELISPOT, lacked the ability to distinguish between individuals with sarcoidosis and individuals with tuberculosis (TB) infection from *Mycobacterium tuberculosis* with or without a positive purified protein derivative (PPD) skin test (also called a tuberculin skin test) or individuals previously vaccinated with BCG (Bacillus Calmette-Guérin), derived from an attenuated strain of *Mycobacterium bovis*. Both of those conditions gave positive reactions to the INFγ-ELISPOT assay (T cell responses to mKatG in 50% of sarcoidosis patients and 50-60% BCG+ or PPD+ subjects). (J. Immunol. (2008) 181:8784-96). In addition, this assay could not distinguish sarcoidosis from individuals with non-tuberculous mycobacterial infection. All of these ailments have disease manifestations that can mimic or overlap with manifestations of sarcoidosis, and thus, these ailments must be excluded before a diagnosis of sarcoidosis can be confirmed.

What is needed is a safer protocol with adequate specificity and sensitivity to assist clinicians in confirming a diagnosis of sarcoidosis.

SUMMARY OF THE INVENTION

Specific microbial proteins, including mycobacterial catalase-peroxidase protein, are found in sarcoidosis tissues and are a target of the immune system of patients with sarcoidosis. Accordingly, diagnostic and prognostic methods are provided, comprising the use of mycobacterial catalase peroxidase protein or derivatives or variants thereof. The protein may be synthesized by recombinant or chemical methods.

The methods may be incorporated into any test format or device suitable for the practice of the methods. Also provided are kits, reagents, etc. for the practice of the methods.

Described herein is a blood test that has a high positive predictive value for confirming a diagnosis of sarcoidosis. The blood test uses, in a first embodiment, *Mycobacterium tuberculosis* catalase-peroxidase (mKatG), and a commercially available mixture of mycobacterial proteins called purified protein derivative (PPD) to stimulate whole blood cells to release an inflammatory cytokine called interferon gamma (INFγ). The INFγ levels from each stimulatory or control condition are measured and the values are applied to an algorithm, which provides data that have been shown to have a high positive predictive value for sarcoidosis. The algorithm is used to predict sarcoidosis, as distinguished from latent or active tuberculosis infection with or without a positive PPD skin test, individuals with a previous vaccination with Bacillus Calmette-Guérin (BCG), individuals with non-tuberculous mycobacterial infection, or individuals with diseases other than sarcoidosis.

The invention is a blood test that can be used to assist in the diagnosis of sarcoidosis. This blood test requires the following specifications in order to operate as a diagnostic test for sarcoidosis: reagents mKatG and PPD purified to certain specifications and used in a specific dose range, the details of which are set forth herein; reagents mKatG, PPD, and a background (no stimulation) used in separate conditions; the use of endotoxin neutralizing agents in the mKatG and PPD conditions; the use of an assay to accurately measure levels of IFNγ in plasma; the use of a defined algorithm that compares the results of INFγ released in the background, mKatG and PPD conditions. The use of a T cell stimulation reagent as a positive control in a separate condition to serve as a quality control measure and assist in the interpretation of whether an individual is capable of responding to the other test conditions (mKatG, PPD) but does not factor into the diagnostic algorithm.

In this embodiment of the invention, the process is a method for aiding in the prediction of whether an individual has sarcoidosis, the method comprising:

(a) treating a first aliquot of blood from the individual as a control having no added INFγ-releasing reagent;

(b) contacting a second aliquot of blood from the individual with fluid containing mKatG in an amount that is ≥0.1 mcg/ml;

(c) contacting a third aliquot of blood from the individual with fluid containing PPD in an amount that is ≥0.1 mcg/ml;

(d) detecting the amount of INFγ in the aliquots;

(e) calculating adjusted amounts of INFγ as amounts of INFγ in the second and third aliquots minus the amount of INFγ in the first aliquot; and (f) associating a prediction of sarcoidosis with the determination that there is (1) an adjusted amount of INFγ for the second aliquot of greater than 100 pg/ml as well as that there is (2) an adjusted amount of INFγ for the second aliquot that is greater than the adjusted amount of INFγ for the third aliquot.

BRIEF DESCRIPTION OF DRAWINGS

FIG. 1 is Table 1, which contains test data for known sarcoidosis and control subjects.

DETAILED DESCRIPTION OF THE INVENTION

Unless defined otherwise above, all technical and scientific terms used herein have the same meaning as commonly understood by one of ordinary skill in the art to which this invention belongs. Where a term is provided in the singular, the inventor also contemplates the plural of that term. The nomenclature used herein and the procedures described below are those well known and commonly employed in the art.

The singular forms "a", "an", and "the" include plural references unless the context clearly dictates otherwise.

The terms "comprise" and "comprising" is used in the inclusive, open sense, meaning that additional elements may be included.

The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of any of the foregoing. The names of the natural amino acids are abbreviated herein in accordance with the recommendations of IUPAC-IUB.

The term "antigenic fragment" refers to a polypeptide fragment or region of a polypeptide that is able to elicit an immune response. An "immune response" refers to the reaction of a subject to the presence of an antigen, which may include at least one of the following: making antibodies, developing immunity, developing hypersensitivity to the antigen, and developing tolerance.

The term "condition" when used with reference to the assay method refers to a sample measurement obtained under particular experimental conditions that differ from the experimental conditions of another sample. Thus when aliquots of patient's blood are exposed to different reagents and then measured for interferon gamma, each of these different measurements obtained as a result of exposure to different reagents or to a control are referred to as a condition; e.g. the mKatG condition, the PPD condition, the background condition.

"Derivative" refers to the chemical modification of a polypeptide sequence, or a polynucleotide sequence. Chemical modifications of a polynucleotide sequence may include, for example, replacement of hydrogen by an alkyl, acyl, or amino group. A derivative polynucleotide encodes a polypeptide which retains at least one biological or immunological function of the natural molecule. A derivative polypeptide is one modified by glycosylation, pegylation, or any similar process that retains at least one biological or immunological function of the polypeptide from which it was derived.

"EU" refers to endotoxin units. Because endotoxin molecular weight may vary a great deal (10,000 to 1,000,000 Daltons), endotoxin is measured in Endotoxin Units (EU). One EU equals approximately 0.1 to 0.2 nanograms of *E. coli* lipopolysaccharide. One assay for measurement of endotoxin is the Limulus amebocyte lysate (LAL) assay. Currently there are at least four forms of the LAL assay, each with different sensitivities. The LAL gel clot assay can detect down to 0.03 EU/mL while the LAL kinetic turbidimetric and chromogenic assays can detect down to 0.005 EU/mL.

The term "microbial catalase or peroxidase protein" refers to any catalase-peroxidase, catalase or peroxidase protein from a microbe, for example, catalase-peroxidase, catalase or peroxidase proteins from mycobacterial species such as *Mycobacterium tuberculosis* and *Mycobacterium smegmatis*, or other bacterial species such as *Helicobacter pylori* and *Propionibacterium acnes*.

The term "non-tuberculous mycobacteria" (NTM) refers to all mycobacterial species other than *Mycobacterium tuberculosis* (Mtb) and includes many common mycobacteria that are closely related to *Mycobacterium tuberculosis*.

The terms "polypeptide fragment" or "fragment," when used in reference to a particular polypeptide, refers to a polypeptide in which amino acid residues are deleted as compared to the reference polypeptide itself, but where the remaining amino acid sequence is usually identical to that of the reference polypeptide. Such deletions may occur at the amino-terminus or carboxy-terminus of the reference polypeptide, or alternatively both. Fragments typically are at least about 5, 6, 8 or 10 amino acids long, at least about 14 amino acids long, at least about 20, 30, 40 or 50 amino acids long, at least about 75 amino acids long, or at least about 100, 150, 200, 300, 500 or more amino acids long. A fragment can retain one or more of the biological activities of the reference polypeptide. In various embodiments, a fragment may comprise an enzymatic activity and/or an interaction site of the reference polypeptide. In another embodiment, a fragment may have immunogenic properties.

A "patient" or "subject" or "host" refers to either a human or non-human animal.

The term "purified" refers to an object species that is the predominant species present (i.e., on a molar basis it is more abundant than any other individual species in the composition). A "purified fraction" is a composition wherein the object species comprises at least about 50 percent (on a molar basis) of all species present. In making the determination of the purity of a species in solution or dispersion, the solvent or matrix in which the species is dissolved or dispersed is usually not included in such determination; instead, only the species (including the one of interest) dissolved or dispersed are taken into account. Generally, a purified composition will have one species that comprises more than about 80 percent of all species present in the composition, in other embodiments more than about 85%, 90%, 95%, 99% or more of all species present. The object species may be purified to essential homogeneity (contaminant species cannot be detected in the composition by conventional detection methods) wherein the composition consists essentially of a single species. A skilled artisan may purify a polypeptide of the invention using standard techniques for protein purification in light of the teachings herein. Purity of a polypeptide may be determined by a number of methods known to those of skill in the art, including for example, amino-terminal amino acid sequence analysis, gel electrophoresis and mass-spectrometry analysis.

The term "PPD" refers to a mixture of mycobacterial proteins known as purified protein derivative. The term "PPD+" refers to a positive Mantoux skin test for tuberculosis, which standardly consists of an intradermal injection of one tenth of a milliliter (mL) of PPD tuberculin.

"Recombinant protein", "heterologous protein" and "exogenous protein" are used interchangeably to refer to a polypeptide which is produced by recombinant DNA techniques, wherein generally, DNA encoding the polypeptide is inserted into a suitable expression vector which is in turn used to transform a host cell to produce the heterologous protein. That is, the polypeptide is expressed from a heterologous nucleic acid.

"Vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops, which, in their vector form are not bound to the chromosome. In the present specification, "plasmid" and "vector" are used interchangeably as the plasmid is a commonly used form of vector. However, as will be appreciated by those skilled in the art, the invention is intended to include such other forms of expression vectors which serve equivalent functions and which become subsequently known in the art.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

In describing alternative embodiments, the inclusion of various embodiments is illustrative and is not intended to limit the invention to those particular embodiments.

Diagnostic Blood Test

The diagnostic blood test for sarcoidosis uses new methodology which improves the diagnostic specificity for sarcoidosis. Prior art in the diagnostic field was unable to sufficiently distinguish between subjects who had sarcoidosis and those subjects with active mycobacterial disease from tuberculosis (TB) or non-tuberculous mycobacteria, or subjects who were PPD+ (latent TB infection), or subjects who had been vaccinated for TB (BCG vaccination). The present inventive method distinguishes sarcoidosis from these and other diseases that are not sarcoidosis.

The diagnostic blood test for sarcoidosis measures release of INFγ from immune cells in blood after contact of the blood cells with the purified reagents mKatG (SEQ ID NO: 2) or PPD (PPD derived from *M. tuberculosis*) or after contact with various control conditions (e.g., no contacting reagent is added or the contacting reagent is not expected to cause release of INFγ). Measurement of INFγ release in response to these reagents provides a specific and sensitive assay. Purifying or neutralizing contaminating endotoxins from the specific reagents mKatG (SEQ ID NO: 2) or PPD reduces nonspecific responses of INFγ release. The diagnostic blood test separately measures release of INFγ from immune cells in blood after contact of the blood cells with a T cell stimulating reagent (positive control) to provide a quality control measure and an assessment of the overall ability of the immune cells in the blood to respond to immune stimulating reagents.

The whole blood test aliquots are combined with test reagents or control reagents and incubated to allow for measurable release of INFγ. Preferably, the incubation is about 12 hours, about 12-18 hrs, or about 12-24 hours. Incubation periods longer than about 24 hours are feasible but not time efficient.

Any suitable method of measuring INFγ is envisioned. Suitability refers to an assay system that is accurate, sensitive, robust and reproducible. Sensitivity of about 4 pg/ml (or the equivalent in International Units (IU) established by using World Health Organization standards) would be suitable. The method should have the capability to recover and measure INFγ in complex fluids such as plasma and serum without interference by confounding serum factors. Examples of measurement methods include ELISA, RIA and multiplex arrays.

The algorithm used in conjunction with the illustrative blood assay states that sarcoidosis is indicated when two circumstances are met: First, the concentration of INFγ in mKatG-stimulated blood minus the concentration of INFγ in blood without a stimulating reagent is greater than 100 pg/ml; second, the concentration of INFγ in mKatG-stimulated blood is greater than the concentration of INFγ in PPD-stimulated blood. (Hereafter, for simplicity, the algorithm will use nomenclature denoting the separate conditions such as mKatG or PPD to mean the concentration of INFγ released in the respective condition measured in pg/ml. The condition of blood without a stimulating reagent will be denoted as background or bkd). Thus, sarcoidosis is indicated when: mKatG minus bkd>100 and mKatG>PPD.

The whole blood stimulation assay algorithm quite accurately predicts persons with sarcoidosis because in most cases the blood of these persons measures higher INFγ release for mKatG stimulation than PPD stimulation (mKatG>PPD) whereas persons who are PPD+, have had BCG vaccination or have active or latent mycobacterial (MTB or non-tuberculous mycobacterial) disease almost always measure higher INFγ for PPD stimulation than for mKatG stimulation (PPD>mKatG). When testing the blood of healthy subjects or those with disease other than sarcoidosis or mycobacterial disease, mKatG stimulation minus background condition (without stimulating reagent) is usually less than 100 pg/ml INFγ (mKatG minus bkd=100), but when mKatG minus background is higher than 100 pg/ml, then PPD>mKatG.

In another embodiment, to adjust the algorithm based on different laboratory conditions, the algorithm can use diagnostic cut-off levels, thresholds, or variables that are determined by testing known sarcoidosis and control subjects, such as shown in Table 1. Furthermore, the thresholds, diagnostic cut-off levels or variables for both conditions of the algorithm can be determined by using standard statistical tests, wherein the sensitivity and specificity of the assay can be increased or decreased and the receiver operating characteristic curves can be used to maximize the diagnostic power of the test in different populations. This is described in more detail below.

In one embodiment, control subjects that do not have sarcoidosis and do not have mycobacterial disease, such as those in the right columns labeled 1-5, can be used to determine a threshold for the first condition of the algorithm. In this embodiment, the first condition of the algorithm is mKatG is greater than the threshold established by testing such control subjects. To further illustrate the use of control subjects, under the laboratory conditions used to establish the data in Table 1, all healthy subjects tested had a mKatG normalized to background below the threshold of 100 pg/ml. Thus, under these conditions the threshold was established at this concentration. Therefore, if different assay conditions were used with the same control subjects and the same sensitivity and specificity was desired, a different threshold could be established.

The variable, Y, in the second condition of the algorithm can be determined by using known control samples, such as those in Table 1. As further illustrated in Table 1, mycobacterial infected control subjects, represented by samples in the right columns labeled 9, 16, 21-28, 32-35, and 37, all have PPD greater than mKatG. Thus, in a preferred embodiment, a variable, Y, can be determined to increase or decrease the value of PPD based on the values detected under different laboratory conditions, such as where different preparations of reagents are used. In another embodiment, Y adjusts the value to a number that is equal to mKatG minus PPD for such controls. Furthermore, non-sarcoidosis disease controls, such as samples in the right columns labeled 1-8, or healthy subjects represented in Table 1 can be used to establish the variable, Y, for the second condition of the algorithm.

Both mKatG and PPD reagents tend to contain considerable endotoxin that cause non-specific elevation in INFγ levels when stimulating whole blood. Endotoxins are not protein antigens that induce adaptive B or T cell immune responses through antigen-specific receptors. Rather, they stimulate the immune system through independent receptor systems found on many types of cells Whole blood stimulation by endotoxin leads to quite variable results in INFγ release between different individuals. Therefore, for the inventive blood test, it is necessary that endotoxins are substantially neutralized as immune system stimulators or are substantially absent from PPD and mKatG preparations. This can be accomplished if the mKatG (SEQ ID NO: 2) and PPD reagents are purified to lower levels of endotoxin by suitable means. As an example, ENDOTRAP® endotoxin-selective affinity chromatography columns accomplish this and have been able to reduce endotoxin levels of PPD to less than 0.10 EU/μg protein. Other suitable means of purification for mKatG are detailed in U.S. Pat. Pub. No. US 2009/0175798.

Purification by any suitable means are envisioned such as by ultrafiltration or various modes of chromatography (e.g., HPLC, reverse phase HPLC or ion exchange).

Due to the charged nature of endotoxins, strong anion exchange chromatography is particularly effective at removing endotoxins (e.g., Q XL resin).

Alternatively, cation exchange chromatography may be utilized in a manner such that positively charged solutes bind to the solid chromatographic media and the endotoxin flows through.

Separations using affinity ligands that bind endotoxin or modified endotoxin binding ligands are also envisioned. Examples include but are not limited to histamine, nitrogen-containing heterocyclic compounds, or polymyxin B.

It is also envisioned to use more than one technique to achieve purification. An example is ENDOTRAP® endotoxin-selective affinity chromatography column with HPLC/FPLC-automated system. Also useful is endotoxin removal resin that combines porous cellulose beads and an FDA-approved food preservative, poly(ε-lysine), as an affinity ligand to selectively bind endotoxins.

As an alternative to purification or in addition to purification, reduction of non-specific elevation in INFγ levels can be accomplished by neutralizing endotoxin in the blood to prevent non-specific stimulation. As an example, polymyxin B (PMX) accomplishes this and the non-specific stimulating effects of contaminating endotoxin are blocked by contacting the blood with PMX before the addition of mKatG (SEQ ID NO: 2) or PPD (both containing endotoxin) in their separate conditions. Without PMX, there can be non-specific stimulation of uncertain magnitude which can vary considerably from person to person whether the amount of endotoxin contained in the added reagents is roughly similar or different.

Neutralizing agents for endotoxin are known and all suitable agents are envisioned, including but not limited to chemicals (e.g., lipopolyamines), proteins (e.g., human lipopolysaccharide-binding protein, hLBP), endotoxin neutralizing peptides (e.g., natural host defense peptides, fragments of lipopolysaccharide ("LPS") binding proteins and engineered peptides), structural classes of cationic amphiphiles, both peptides and non-peptidic small molecules. Examples include antimicrobial peptides, such as the skin antimicrobial peptides of the southern bell frog, LPS binding peptides, such as Li5-001, having the amino acid sequence KNYSSSISSIHAC (SEQ ID NO: 1), or the dodecapeptide, Li5-025 having amino acid sequence K'YSSSISSIRAC', wherein K' and C' are D-forms of K and C, respectively (Matsumoto et al., 2010. J. Microbiol. Methods. 82, 54-58). Typical examples of endotoxin binding ligands include histamine, nitrogen-containing heterocyclic compounds, and polymyxin B. Also included are herbs (e.g., *Gardenia* jasminoides Ellis) or their bioactive components that have endotoxin neutralizing activity (e.g., geniposide).

As an alternative to purification or in addition to purification, reduction of non-specific elevation in INFγ levels can be accomplished by neutralizing endotoxin in the blood to prevent non-specific stimulation. As an example, polymyxin B (PMX) accomplishes this and the non-specific stimulating effects of contaminating endotoxin are blocked by contacting the blood with PMX before the addition of mKatG or PPD (both containing endotoxin) in their separate conditions. Without PMX, there can be non-specific stimulation of uncertain magnitude which can vary considerably from person to person whether the amount of endotoxin contained in the added reagents is roughly similar or different.

Neutralizing agents for endotoxin are known and all suitable agents are envisioned, including but not limited to chemicals (e.g., lipopolyamines), proteins (e.g., human lipopolysaccharide-binding protein, hLBP), endotoxin neutralizing peptides (e.g., natural host defense peptides, fragments of LPS binding proteins and engineered peptides), structural classes of cationic amphiphiles, both peptides and non-peptidic small molecules. Examples include antimicrobial peptides, such as the skin antimicrobial peptides of the southern bell frog, LPS-binding peptides, such as Li5-001, having the amino acid sequence KNYSSSISSIHAC, or the dodecapeptide, Li5-025 having amino acid sequence K'YSSSISSIRAC', wherein K' and C' are D-forms of K and C, respectively (Matsumoto et al., 2010. J. Microbiol. Methods. 82, 54-58). Typical examples of endotoxin binding ligands include histamine, nitrogen-containing heterocyclic compounds, and polymyxin B. Also included are herbs (e.g., *Gardenia jasminoides* Ellis) or their bioactive components that have endotoxin neutralizing activity (e.g., geniposide).

In general, without added endotoxin neutralizing agent, endotoxin measurement in the blood conditions without added reagents should be down to 0.25-1.0 EU/ml, preferably 0.1-0.25 EU/ml, and more preferably less than 0.1 EU/ml to be substantially neutralized. Measurement less than 0.01 EU/ml is most preferable and is considered endotoxin free.

Endotoxin measurements for PPD preparations should be down to 0.25-1.0 EU per microgram of protein, preferably 0.1-0.25 EU per microgram, more preferably 0.01-0.10 EU per microgram and even more preferably <0.01 EU per microgram to be substantially neutralized. Endotoxin measurements in the blood condition with PMX added as a neutralizing agent followed by addition of PPD should be down to 1.5-10 EU per ml, preferably 1.0-1.5 EU per ml, more preferably 0.50-1.0 EU/ml, even more preferably 0.10-0.50 EU per ml and even more preferably <0.10 EU per ml to be substantially neutralized. Endotoxin measurements in the blood condition with PMX added as a neutralizing agent followed by addition of mKatG should not be greater than 200 EU per ml, preferably 100-200 EU per ml, more preferably 50-100 EU per ml and even more preferably 10-50 EU per ml to be substantially neutralized. Prior purification of mKatG reagent that results in the level of endotoxin below 10 EU per ml when added to the whole blood condition may degrade the stimulatory potency of mKatG and are less preferable than 10-50 EU per ml.

There are many sources of endotoxin contamination in the laboratory. Water is perhaps the greatest source of contamination. High purity water is absolutely essential. Endotoxin can adhere strongly to glassware and plastics unless decontaminated by the inactivation of endotoxin. Other potential sources of endotoxin contamination are worker's fingers, chemical reagents, raw materials, and buffers.

If the blood test were performed in a laboratory where unpredictable endotoxin effects were apparent, this would alter the test results and degrade operating characteristics of the test.

If the blood test is adjusted to optimize receiver operating characteristics (ROC), then the amount (dose) of mKatG and PPD that are added to each 1-ml condition is subject to change. It is contemplated that the sarcoidosis blood test dose for mKatG and PPD results in a final concentration of 0.1-50 microgram/ml in each respective condition. Preferably, the dose for mKatG and PPD results in a final concentration of 0.5-20 micrograms/ml. More preferably, the dose for mKatG and PPD results in a final concentration of 1.0-10 micrograms/ml. Still more preferably, the dose for mKatG and PPD results in a final concentration of 1-5 micrograms/ml. Most preferably, the dose for mKatG results in a final concentration of 2 micrograms/ml, and the dose for PPD results in a final concentration of 5 micrograms/ml.

If the blood test is adjusted to optimize receiver operating characteristics (ROC), then the INFγ levels in the algorithm are subject to change. In a preferred embodiment, the levels can be adjusted to reach a desired sensitivity and specificity. A positive test for sarcoidosis requires meeting both the specification that mKatG minus bkd>100 pg/ml INFγ and the specification that concentration of INFγ in mKatG condition is greater than the concentration of INFγ in the PPD condition. Taking the first specification, a slight deviation from the algorithmic value of 100 would not change the prediction but a large deviation would. For example, a threshold level of 101 or 99 instead of 100 would not materially change the sensitivity or specificity of the test. Large deviations from the threshold level of 100 (e.g. where mKatG minus bkd>200 for sarcoidosis diagnosis) would materially affect the sensitivity and specificity of the test. In general, levels of INFγ much greater than 100 pg/ml would reduce test sensitivity but increase test specificity for a positive sarcoidosis diagnosis. For example, an algorithm using a level of 200 pg/ml INFγ for mKatG minus background may increase specificity to 100% but decrease sensitivity because of the greater response needed to meet this threshold. In general, levels of INFγ much lower than 100 pg/ml would reduce test specificity but increase sensitivity for a positive sarcoidosis diagnosis. It is contemplated that the algorithm value for mKatG minus background is greater than 10 pg/ml. More preferably, the algorithm value for mKatG minus background is greater than 80 pg/ml. Still more preferably, the algorithm value for mKatG minus background is greater than 500 pg/ml. Even more preferably, the algorithm value for mKatG minus background is greater than 200 pg/ml. Most preferably, the algorithm value for mKatG minus background is greater than 100 pg/ml IFNγ.

The second specification that mKatG>PPD for a sarcoidosis diagnosis is designed to differentiate between sarcoidosis and mycobacterial infected individuals or those who have had BCG vaccination. A slight deviation from this specification on either side of the unequal sign would not change the prediction. For example, the specification that mKatG is greater than PPD plus 1 pg/ml INFγ or mKatG plus 1 pg/ml INFγ is greater than PPD (i.e., mKatG>PPD minus 1 pg/ml) would not materially affect the results. A large deviation from this specification would significantly affect test characteristics and its diagnostic performance. For example, a specification that a sarcoidosis diagnosis requires mKatG>(PPD+400 pg/ml (or more)) will decrease sensitivity but increase specificity since the higher threshold for mKatG makes it more difficult for a sarcoidosis diagnosis. An example that modifies the algorithm to mKatG>(PPD minus 400 pg/ml (or more)) will increase test sensitivity but significantly reduce specificity. Deviations between these extremes may provide optimal test characteristics. In some examples, mKatG>(PPD+50 pg/ml) or mKatG>(PPD minus 20 pg/ml) might produce the optimal test characteristics. It is contemplated that the algorithm for a sarcoidosis diagnosis requires the condition mKatG>PPD+300 pg/ml or the condition that mKatG>PPD minus 300 pg/ml. More preferably, it is contemplated that the algorithm for a sarcoidosis diagnosis requires the condition mKatG>(PPD+100 pg/ml) or the condition mKatG>(PPD minus 100 pg/ml). Even more preferably, it is contemplated that the algorithm for a sarcoidosis diagnosis requires the condition mKatG>(PPD+50 pg/ml) or the condition mKatG>(PPD minus 50 pg/ml). Still more preferably, it is contemplated that the algorithm for a sarcoidosis diagnosis requires the condition mKatG>(PPD+20 pg/ml) or the condition mKatG>(PPD minus 20 pg/ml). Most preferably, it is contemplated that the algorithm for a sarcoidosis diagnosis requires the condition mKatG>PPD.

Thus, taking into consideration variability when conducting testing in different laboratories, a more universal algorithm to apply for a sarcoidosis diagnosis would use the value that mKatG minus background is greater than 10 pg/ml IFNγ; and mKatG is greater than PPD+300 pg/ml IFNγ or mKatG is greater than PPD minus 300 pg/ml IFNγ. These considerations as to laboratory variability then, as applied to the entire blood assay test would require a more universal algorithm that sarcoidosis is indicated when:

1. mKatG minus background is greater than 10 pg/ml IFNγ.
2. mKatG is greater than (PPD plus 300 pg/ml IFNγ), or mKatG is greater than (PPD minus 300 pg/ml IFNγ).

For this universal algorithm to be have the test characteristics desired for a diagnostic test, then also:

3. mKatG amount added to 1 ml blood: ≥0.1 mcg/ml.
4. PPD amount added to 1 ml blood: ≥0.1 mcg/ml.

The inventive diagnostic blood test for sarcoidosis includes a separate condition where a T cell stimulating reagent is added to blood to provide a positive control condition. This condition does not affect the universal algorithm described above. The specific type of T cell stimulating reagent used in the assay is not critical as long as the reagent stimulates a large fraction of T cells. Generally, the T cell stimulating reagent should stimulate more than 10% of T cells circulating in blood of healthy individuals and more than about 20%, 30%, 50%, 70% or more of all T cells present. A skilled artisan may use a T cell stimulating reagent including (but not limited to) reagents such as toxins that stimulate T cells through binding to specific T cell receptor proteins (e.g. Staphylococcal enterotoxin B or A), mitogens such as phytohaemagglutinin or phorbol myristate acetate (PMA), or antibodies to specific surface receptors on T cells (e.g., anti-CD3) or a combination of reagents. This condition provides an essential quality control measure and assists in the interpretation of whether an individual is capable of responding to the other test conditions (mKatG, PPD). For example, a low level of INFγ released in the positive control would indicate that a negative test may be the result of incorrect blood handling or an individual who is immunosuppressed. In another example, if the level of IFNγ released in the background, mKatG or PPD conditions approaches the level of INFγ released in the positive T cell control condition, this would lead the test result to be discarded because of the possibility of reagent or culture contamination. (Since mKatG and PPD contain a limited number of immune stimulating fragments and thus, would only stimulate a small fraction (<20% and typically much lower than 20%) of circulating blood T cells, the release of INFγ in the mKatG and PPD conditions would not be expected to approach the amount of INFγ released in a positive control condition that stimulates a large fraction of T cells). It is contemplated that if the INFγ released in the background, mKatG or PPD conditions is greater than 20%, preferably 50%, more preferably 60%, most preferably 80% or greater of the positive control, the test result would be discarded with a recommendation to repeat the test.

The mycobacterial catalase-peroxidase protein used in the blood test may be from various species of mycobacteria (e.g. *Mycobacterium tuberculosis, Mycobacterium smegmatis, Propionibacterium acnes, Helicobacter pylori*) or may include active fragments, fusion proteins or modified protein. Alternative species of the protein are described in U.S. Pat. Pub. No. US 2009/0175798.

In the examples shown below, a full length recombinant mKatG was used in the blood tests. The recombinant mKatG is slightly modified from the precise gene sequence of *Mycobacterium tuberculosis* due to cloning in the vector which adds amino acids.

Microbial Catalase or Peroxidase Protein Composition

Specific microbial proteins in sarcoidosis tissues, mycobacterial catalase-peroxidase proteins, are targets of the immune system of patients with sarcoidosis. Thus, provided are isolated recombinant and/or purified microbial catalase or peroxidase polypeptides.

In one embodiment, the polypeptide comprises a sequence having at least about 90%, preferably about 95%, more preferably about 96%, still more preferably about 97%, still more preferably about 98%, yet more preferably about 99% and most preferably about 100% sequence homology to the sequence of *Mycobacterium tuberculosis* KatG (SEQ ID NO: 2) as described in U.S. Pat. Publication No. US 2009/0175798, or to a fragment thereof, e.g., an antigenic fragment. The mKatG (SEQ ID NO: 2) is 740 amino acids in length. A blood test is contemplated that uses large antigenic fragments of mKatG as antigens. The fragments that are contemplated are the fragments of amino acids 1-631, preferably amino acids 1-672 and most preferably amino acids 1-705. In another embodiment the contemplated fragment is amino acids 5-470 and preferably amino acids 5-631. These ranges include a large majority of potential antigenic peptides within the full length mKatG. For example, it is likely that a portion of the full length mKatG (SEQ ID NO: 2) that contains 90% of peptide fragments known to bind to some polymorphic MHC molecules would provide sufficient antigenic stimulation in 90% or so of sarcoidosis patients.

Blood Test as Biomarker

The inventive blood test described in this application may also serve as a prognostic tool to predict the likelihood of the subsequent clinical course of sarcoidosis, for example, whether the course of sarcoidosis has undergone remission (where the inflammation subsides and anti-inflammatory treatment is not needed) or whether the sarcoidosis is chronic with persistent or progressive disease. Further included is using the inventive blood test as a monitor of disease "activity". Active disease is generally meant to include persistent or worsening symptoms and/or laboratory or clinical imaging studies that indicate the presence of ongoing or progressive inflammation.

In one embodiment, individuals with sarcoidosis who have a positive diagnostic blood test on initial testing for sarcoidosis will have a repeat test in follow-up during their clinical course. Those individuals who are not on treatment and have a negative test (mKatG minus bkd<100) would predict that the disease is in remission and does not need treatment. In this situation, if this blood test turns positive (mKatG minus bkd>100) in further future testing, this would indicate a return of active disease. In another embodiment, this inventive blood test can be used to assess whether a prescribed treatment (using therapies including but not limited to corticosteroids, immunosuppressive and anti-TNF therapies) is effective and being used in an adequate dose to suppress disease activity. For those individuals who are on treatment (and had a positive initial blood test), a negative blood test (mKatG minus bkd<100) indicates that treatment is currently adequate in suppressing disease activity. Individuals with sarcoidosis who are being treated and have a positive repeat blood test (mKatG minus bkd>100) indicates the treatment is ineffective or being used in an inadequate dose. This inventive blood test may be particularly useful in sarcoidosis to assess adequacy of treatment when patients are being tapered on their corticosteroid or other anti-inflammatory treatments i.e., a positive test indicates active disease that needs additional treatment, whereas a negative test supports the adequacy of the current level of treatment.

If the inventive blood test used for these purposes is adjusted to optimize receiver operating characteristics (ROC), then the INFγ levels in the algorithm are subject to change. For the use of this blood test for these purposes, it is contemplated that the algorithm value for mKatG minus background is greater than 10 pg/ml IFNγ. More preferably, the algorithm value for mKatG minus background is greater than 80 pg/ml IFNγ. Still more preferably, the algorithm value for mKatG minus background is greater than 500 pg/ml IFNγ. Even more preferably, the algorithm value for mKatG minus background is greater than 200 pg/ml IFNγ. Most preferably, the algorithm value for mKatG minus background is greater than 100 pg/ml IFNγ.

Such a test may be employed at multiple times during the clinical course of sarcoidosis. This test may be used together with other patient information derived from tests including but not limited to genetic tests, proteomic profiles of tissues or blood, or other tests of general immunity in sarcoidosis patients, in order to enhance the test characteristics as a diagnostic tool or as an aid in clinical management.

The following examples set forth the general procedures involved in practicing the present invention. To the extent that specific materials are mentioned, it is merely for purposes of illustration and is not intended to limit the invention.

EXAMPLE 1

Blood Test Methodology

Patients with biopsy-proven sarcoidosis and control subjects (including PPD+, BCG+ controls and subjects undergoing bronchoscopy) were recruited with informed consent and IRB approval. A whole blood stimulation INFγ-release assay was tested using full-length recombinant (rec)-mKatG and PPD as antigens. INFγ-release after 24 hrs was measured by ELISA in each condition and in a separate background control condition in which culture media was added. Staphylococcal enterotoxin B (Toxin Technology) was used as a positive control. Following pilot studies assessing optimal doses and conditions, a sarcoidosis diagnosis was determined by the following results: mKatG minus media (bkd)>100 pg/ml and mKatG>PPD.

MATERIALS AND METHODS

Study Population

Clinical samples were obtained from patients with sarcoidosis, healthy subjects, patients with non-sarcoidosis lung disease or other systemic inflammatory diseases recruited from specialized clinics or hospitals of the Johns Hopkins University. A diagnosis of sarcoidosis was established either by tissue biopsy or by initial manifestations consistent with Lofgren syndrome (erythema nodosum and/or acute arthritis, hilar lymphadenopathy) without alternative diagnoses according to world-wide consensus criteria. Based on clinical manifestations, chest radiograph, and pulmonary function tests, patients were classified as having active sarcoidosis or "inactive" disease, defined by resolution of disease manifestations or absence of disease progression off all therapy for at least 1 year. Untreated patients were those who had not received systemic therapy within 3 months of the time of study. Control subjects included healthy individuals with documented skin testing to purified protein derivative (PPD) within the past year or with a self-reported prior history of BCG vaccination. PPD skin testing was performed in accordance with accepted criteria used in the respective countries. All study subjects participated voluntarily and provided informed consent under protocols approved by the local institutional review board.

Reagents

Complete medium was made from RPMI (Cellgro Mediatech Inc.), 10% pooled human AB serum (Sigma-Aldrich), 1% penicillin-streptomycin (Biosource), 1% Sodium Pyruvate (Sigma), 1% Non-essential amino acids (Gibco), 2.5% Hepes buffer (Quality Biological).

Recombinant Mtb KatG protein was isolated and prepared using an *E. coli* UM255 strain overexpression system carrying a plasmid construct pYZ56 containing the wild-type *M. tuberculosis* katG gene in a 2.9 kD EcoRV-KpnI fragment in pUC19 vector (Zhang et al, Nature (1992) 358:591-593) and as published in Chen et al. J Immunol. (2008); 181:8784-96. PMID: 19050300. The culture was grown in LB medium containing 100 µg/ml ampicillin and agitated overnight at 37° C. The cells were harvested by centrifugation at 4000 g for 15 min at 4° C. Cell pellets were resuspended in 100 ml of 10 mM phosphate buffer ($Na_2HPO_4$ and $NaH_2PO_4$ and 0.5 mM EDTA) (pH 6.0) and sonicated with three 30 s bursts at full power. Insoluble material was removed by centrifugation at 12000 g, 4° C. for 30 min. The supernatant was harvested for further purification by ammonium sulfate precipitation, and the protein was harvested by centrifugation at 12000 g for 30 min. The pellet was resuspended in the phosphate buffer and dialyzed against the same buffer at 4° C. overnight and then assayed for peroxidase and catalase activity. The active fractions were further purified by gel filtration chromatography. A SUPERDEX® 200 gel filtration column (Pharmacia) was equilibrated with the phosphate buffer overnight. The catalase containing fractions were loaded onto the column with a flow rate of 0.2 ml/min. Fractions (1 ml) were collected, and assayed for peroxidase and catalase activity. Active fractions were assessed for purity by SDS-PAGE, pooled, and then dialyzed against the above phosphate buffer at 4° C. overnight (Johnsson, K. et al. J Biol Chem (1997) 272:2834-2840). The purified KatG protein was at least 95% pure. The protein was kept at −80° C. for long term storage and −20° C. for short term (<2 months) between immunological studies.

PPD was obtained from Staten Serum Institut. The PPD was further purified by ENDOTRAP® Endotoxin Removal Kit (Hyglos, Germany) using 3 flow through passes following manufacturer's recommendations.

Staphylococcal enterotoxin B (SEB) was purchased from Toxin Technology. Cells were stimulated with either recombinant mKatG or PPD (Staten Serum Institut), or with Staphylococcal enterotoxin B (SEB) (Toxin Technology) as a positive control.

Whole Blood IFNγ Release Assay

Briefly, whole blood was obtained by phlebotomy and placed into a heparinized tube. The blood was mixed by pipetting up and down 5 times, and then 1 ml aliquots of whole blood were added to individual 5 ml polypropylene snap-cap round bottom tubes. Reagents were added to individual tubes: 10 µl of complete media (or no added media), PMX final 10 µg/ml, mKatG plus PMX 10 µg/ml, PPD plus PMX 10 µg/ml and SEB 1 µg/ml. The tubes were lightly vortexed and incubated at 37° C. in a humidified $CO_2$ incubator for 24 hr. with loose snap caps. After 24 hrs, the plasma layer was harvested by pipette, transferred to microfuge tubes with 25-40 µl of EDTA per plasma sample, centrifuged 1000×g for 3 minutes to pellet blood cells, the plasma transferred to a second set of microfuge tubes with 20 µl of EDTA, centrifuged again and then the plasma was transferred to a clean microfuge for storage at −80 deg Celsius until measurement of INFγ levels. INFγ levels were measured by ELISA (BioLegend) following manufacturer's protocol.

Statistics

Statistical analyses were performed Fisher's exact test or with chi-square analysis and ROC curve generation was performed using GraphPad Prism 5 (GraphPad Software).

Results

TABLE 2

SUMMARY OF ASSAY RESULTS

| rec mKatG/PPD assay | Pos | Neg | Total | Test Results Sensitivity | Specificity |
|---|---|---|---|---|---|
| Active Sarcoidosis,untreated | 20 | 11 | 31 | 65% | |
| Controls | 1 | 40 | 41 | | 98% |
| BCG+, PPD+ or NTM | 0 | 16 | 16 | | 100% |

We explored the operating characteristics of this test using recombinant-mKatG and PPD. Using 2 µg/ml recombinant-mKatG and criteria above, 20/31 (65%) sarcoidosis patients were positive for a sarcoidosis diagnosis vs. 1/41 (98%) controls (Fisher's exact test, p<0.0001). All 16 BCG+ or PPD+ subjects or patients with non-tuberculous mycobacterial infection were negative for a sarcoidosis diagnosis. These data indicate the test has a sensitivity of 65%, a specificity of 98%, a positive predictive value of 95%, a negative predictive value of 79% and a likelihood ratio of 26.45. The confidence interval for the positive predictive value of this test is 0.7618 to 0.9988.

These results suggest a whole blood serum INFγ-release assay using mKatG and PPD has a high positive predictive value for sarcoidosis.

EXAMPLE 2

Processing of Whole Blood Samples for 24 hr Plasma Collection
1. Label all sterile polypropylene cell culture tubes with Subject No. and condition.
2. Uncap 1 heparinized tube of whole blood. Pipet up and down (5×) with an individually wrapped sterile 5 ml serological pipet for mixing.
3. Set up sterile 5 ml polypropylene, snap-cap, round bottom tubes.
4. Add 1 ml whole blood from heparinized tube using individually wrapped 1 ml sterile serological pipet directly to each respective empty tube.
5. Add reagents as specified below to appropriate tubes beginning with PMX first, followed by mKatG, PPD and then Staphylococcal enterotoxin B (SEB).
Test Conditions:
A. No addition (bkd)
B. PMX 10 µg/ml
C. mKatG (optimal dose(s) may vary dependent on test conditions; in experiments shown here: (2 µg/ml)+PMX 10 µg/ml (added first).
D. PPD (5 µg/ml)+PMX 10 µg/ml (added first).
E. SEB-(1 µg/ml) 1 µl from stock (positive control)
6. Lightly (pulse) vortex each tube to mix whole blood. Place all test conditions in 37° C./5% $CO_2$ incubator for 24 hrs with loose snap-caps.
7. After 24 hrs, remove tubes from incubator and note the plasma layer residing above the cellular layer of blood. Leave plasma layer undisturbed.
8. PLASMA HARVEST and TRANSFER: 2 transfers to clean the plasma before storage:
9. Set up two sets of microcentrifuge tubes in a tube rack, numbered 1-10. The two sets are for sequential transfers of the plasma.
10. Add 25-40 µl (1:10 EDTA per plasma sample) of 20 mM EDTA to the $2^{nd}$ set of microcentrifuge tubes for the final transfer.
11. Carefully transfer plasma (using a 200 µl pipet) usually 2 pipet fills of 200 µl or more) from the original stimulation tube to the $1^{st}$ set of 1.5 ml microcentrifuge tubes. (Avoid drawing blood into the plasma). Collect the "clean" plasma, an average of 300-500 µl.
12. Spin microcentrifuge tubes at 1000×g for 3 minutes.
13. Transfer plasma, (leave whole blood pellet undisturbed) into the $2^{nd}$ set of microcentrifuge tubes with the EDTA. (the final concentration of EDTA is about 2 mM and prevents clotting in the samples).
14. Store samples at −80° C.
15. For subsequent ELISA runs, dilute the thawed samples 1:4 with the ELISA diluent for INFγ. Discard any clots that may form in the samples.

Each sample is measured for concentration of INFγ by ELISA (INFγ ELISA kit, BioLegend, San Diego, Calif.).

Reagents for use in the above procedure:
1. none
2. PMX (Polymyxin B; Sigma-Aldrich) commercially available.
3. recombinant mKatG prepared as described in: Chen E S, et at J Immunol. 2008; 181:8784-96.
4. Purified protein derivative (PPD) (from Staten Serum Institut, Denmark). This is further purified using commercially purchased ENDOTRAP® endotoxin-selective affinity chromatography columns to reduce endotoxin levels to <0.10 EU/microgram.
5. Staphylococcal enterotoxin B (SEB) commercially purchased, positive control.

The algorithm used to compare the results is the following: the INFγ concentration in the mKatG condition minus the INFγ concentration in the background condition is greater than 100 pg/ml and the INFγ concentration in the mKatG condition is greater than the INFγ concentration in the PPD condition. For a positive test for sarcoidosis, both specifications must be present. Otherwise, the result is nondiagnostic.

In the experiments described above, an mKatG dose of 2 µg/ml and a PPD dose of 5 µg/ml, and the cut-off thresholds provided in the algorithm (INFγ levels of mKatG minus background>100 pg/ml and mKatG>PPD for a positive test for sarcoidosis) optimize the positive predictive value of the blood test

REFERENCES

All publications and patents mentioned herein are hereby incorporated by reference in their entirety as if each individual publication or patent was specifically and individually incorporated by reference. In case of conflict, the present application, including any definitions herein, will control.

---

What is claimed is:

1. A kit for diagnosing sarcoidosis comprising:
   a first blood collection tube including a first composition comprising an endotoxin neutralizing agent and an isolated microbial catalase-peroxidase comprising at least amino acids 5-470 of SEQ ID NO: 2;
   a second blood collection tube including a second composition comprising an endotoxin neutralizing agent and purified protein derivative of *Mycobacterium tuberculosis* (PPD); and
   optionally instructions.

2. The kit of claim 1, further comprising a third composition comprising a T-cell stimulating re